United States Patent

Kraatz et al.

Patent Number: 6,004,992
Date of Patent: Dec. 21, 1999

[54] AMINOCARBOXYLIC ACID FLUOROBUTENYL ESTERS

[75] Inventors: Udo Kraatz, Leverkusen; Wolfram Andersch, Bergisch Gladbach; Andreas Turberg, Haan; Norbert Mencke, Leverkusen, all of Germany

[73] Assignee: Bayer Aktiengesellschaft, Leverkusen, Germany

[21] Appl. No.: 09/077,259

[22] PCT Filed: Nov. 18, 1996

[86] PCT No.: PCT/EP96/05076

§ 371 Date: May 22, 1998

§ 102(e) Date: May 22, 1998

[87] PCT Pub. No.: WO97/19599

PCT Pub. Date: Jun. 5, 1997

[30] Foreign Application Priority Data

Nov. 30, 1995 [DE] Germany .................. 195 44 674

[51] Int. Cl.$^6$ ............ A61K 31/24; C07C 69/74; C07C 69/716; C07D 209/09
[52] U.S. Cl. ............ 514/423; 514/540; 514/613; 548/530; 548/540; 560/41; 560/51; 560/174
[58] Field of Search .................. 514/423, 540, 514/613; 548/530, 540; 560/41, 51, 174

[56] References Cited

U.S. PATENT DOCUMENTS

| | | | |
|---|---|---|---|
| 4,950,666 | 8/1990 | Peake et al. | 514/227.5 |
| 4,952,580 | 8/1990 | Martinez et al. | 514/236.2 |
| 5,081,287 | 1/1992 | Peake et al. | 560/219 |

FOREIGN PATENT DOCUMENTS

| | | |
|---|---|---|
| 0 432 861 | 6/1991 | European Pat. Off. |
| WO 92/15 555 | 9/1992 | WIPO. |

OTHER PUBLICATIONS

Chemical Abstract 119, 94 942 "Preparation of Fluoroalkenyl group–containing compounds as pesticides" Sep. 16, 1992.

Houben–Weyl, Methoden der organischen Chemie, Georg Thieme Verlag, Stuttgart, 1974, vol. XV/1, p. 315 f.

Houben–Weyl, Methoden der organischen Chemie, Georg Thieme Verlag, Stuttgart, 1974, vol. XV/1, p. 46 ff.

*Primary Examiner*—Johann Richter
*Assistant Examiner*—Jane C. Osweсki
*Attorney, Agent, or Firm*—Sprung Kramer Schaefer & Briscoe

[57] ABSTRACT

The present invention relates to novel fluorobutenyl aminocarboxylates of the formula (I)

$$R—CO—O—CH_2—CH_2—CX=CF_2 \qquad (I)$$

in which

X represents hydrogen or halogen and

R represents one of the groups

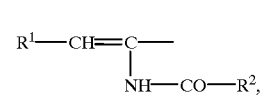
(a)

(b) $R^3—A—CO—NR^4—CR^5R^6—$ or

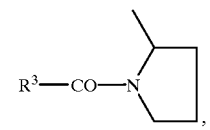
(c)

in which

A, $R^1$, $R^2$, $R^3$, $R^4$, $R^5$ and $R^6$ are each as defined in the description, to processes for their preparation and to their use for controlling animal pests.

4 Claims, No Drawings

AMINOCARBOXYLIC ACID FLUOROBUTENYL ESTERS

This application is a 371 of PCT/EP96/05076 filed Nov. 18, 1996.

The present invention relates to novel fluorobutenyl aminocarboxylates, to processes for their preparation and to their use for controlling animal pests, in particular insects, arachnids and nematodes, encountered in agriculture, in forests, in the protection of stored products and of materials, and in the hygiene sector.

It is already known that certain fluoroalkenyl compounds have insecticidal, acaricidal and nematicidal activity (cf. for example WO 92/15 555, U.S. Pat. No. 4,952,590, U.S. Pat. No. 4,950,666, U.S. Pat. No. 3,914,251). However, the efficacy and the activity spectrum of these compounds, in particular at low application rates and concentrations, is not always entirely satisfactory.

This invention, accordingly, provides novel fluorobutenyl aminocarboxylates of the formula (I)

R—CO—O—CH$_2$—CH$_2$—CX=CF$_2$     (I)

in which
X represents hydrogen or halogen and
R represents one of the groups

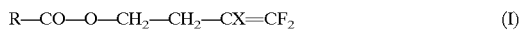

(a)

(b) R$^3$—A—CO—NR$^4$—CR$^5$R$^6$— or

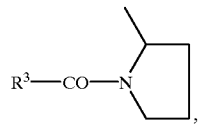

(c)

in which
R$^1$ represents respectively optionally substituted alkyl, aryl or hetaryl,
R$^2$ represents hydrogen, alkyl, halogenoalkyl or optionally substituted aryl,
R$^3$ represents hydrogen, alkyl, halogenoalkyl, alkenyl, alkoxy, halogenoalkoxy, alkylthio, halogenoalkylthio or respectively optionally substituted aralkyloxy or aryl,
R$^4$, R$^5$ and R$^6$ independently of one another each represent hydrogen, alkyl or respectively optionally substituted aralkyl or aryl, or
R$^5$ and R$^6$ together represent optionally substituted alkanediyl and
A represents a direct bond or represents NH.

Taking into account the various meanings of group R, the following structures are obtained:

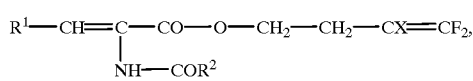

(Ia)

R$^3$—A—CO—NR$^4$—CR$^5$R$^6$—CO—O—CH$_2$—CH$_2$—CX=CF$_2$ and (Ib)

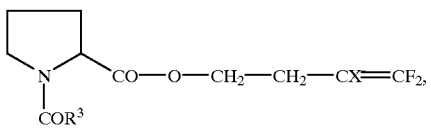

(Ic)

in which
R$^1$, R$^2$, R$^3$, R$^4$, R$^5$, R$^6$, A and X are each as defined above.

The compounds of the formula (I) can be present as geometric and/or optical isomers, or isomer mixtures of varying compositions, depending inter alia on the nature of the substituents. The invention provides both the pure isomers and the isomer mixtures.

Furthermore, it has been found that, (A) the compounds of the formula (Ia) are obtained when azlactones of the formula (II)

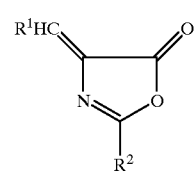

(II)

in which
R$^1$ and R$^2$ are each as defined in claim 1
are reacted with alcohols of the formula (III)

CF$_2$=CX—CH$_2$—CH$_2$—OH     (III)

in which
X is as defined above,
in the presence of a diluent and, if appropriate, in the presence of a base, (B) the compounds of the formula (Ib) are obtained when α) acylated amino acids of the formula (IV)

R$^3$—A—CO—NR$^4$—CR$^5$R$^6$—COOH     (IV)

in which
A, R$^3$, R$^4$, R$^5$ and R$^6$ are each as defined above
are reacted with alcohols of the formula (III)

CF$_2$=CX—CH$_2$—CH$_2$—OH     (III)

in which
X is as defined above,
if appropriate in the presence of a diluent and in the presence of a reactive reagent, or β) azlactones of the formula (V)

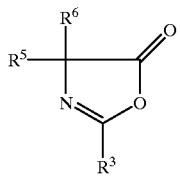
(V)

in which
R$^3$, R$^5$ and R$^6$ are each as defined above
are reacted with alcohols of the formula (III)

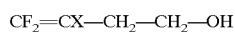
CF$_2$=CX—CH$_2$—CH$_2$—OH   (III)

in which
X is as defined above,
in the presence of a diluent and, if appropriate, in the presence of a base, and (C) compounds of the formula (Ic) are obtained when acylated amino acids of the formula (VI)

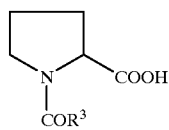
(VI)

in which
R$^3$ is as defined above
are reacted with alcohols of the formula (III)

CF$_2$=CX—CH$_2$—CH$_2$—OH   (III)

in which
X is as defined above,
if appropriate in the presence of a diluent and in the presence of a reactive reagent.

Finally, it has been found that the novel fluorobutenyl aminocarboxylates of the formula (I) have pronounced biological properties and are suitable especially for controlling animal pests, in particular insects, arachnids and nematodes, encountered in agriculture, in forests, in the protection of stored products and of materials, and in the hygiene sector.

The formula (I) provides a general definition of the fluorobutenyl aminocarboxylates according to the invention.

Preferred substituents or ranges of the radicals listed in the formulae mentioned hereinabove and hereinbelow are illustrated below:

X preferably represents hydrogen, fluorine or chlorine.

R preferably represents one of the groups (a)
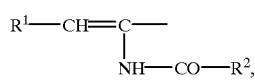
R$^1$—CH=C—
           |
           NH—CO—R$^2$, (b) R$^3$—A—CO—NR$^4$—CR$^5$R$^6$— or (c)
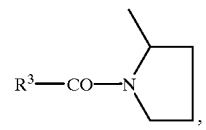
R$^3$—CO—N R$^1$ preferably represents C$_1$–C$_6$-alkyl or phenyl which is optionally mono- to trisubstituted by identical or different substituents from the group consisting of halogen, C$_1$–C$_6$-alkyl, C$_1$–C$_4$-halogenoalkyl, C$_1$–C$_6$-alkoxy, C$_1$–C$_4$-halogenoalkoxy, C$_1$–C$_6$-alkylthio, C$_1$–C$_4$-halogenoalkylthio, cyano, nitro and SCN, or preferably represents thienyl, furanyl or pyridyl, each of which is optionally mono- or disubstituted by identical or different substituents from the group consisting of halogen and C$_1$–C$_4$-alkyl.

R$^2$ preferably represents hydrogen, C$_1$–C$_6$-alkyl, C$_1$–C$_6$-halogenoalkyl, or preferably represents phenyl which is optionally mono- to trisubstituted by identical or different substituents from the group consisting of halogen, C$_1$–C$_6$-alkyl, C$_1$–C$_4$-halogenoalkyl, C$_1$–C$_6$-alkoxy, C$_1$–C$_4$-halogenoalkoxy, C$_1$–C$_6$-alkylthio, C$_1$–C$_4$-halogenoalkylthio, cyano, nitro and SCN.

R$^3$ preferably represents hydrogen, C$_1$–C$_6$-alkyl, C$_1$–C$_4$-halogenoalkyl, C$_2$–C$_6$-alkenyl, C$_1$–C$_6$-alkoxy, C$_1$–C$_4$-halogenoalkoxy, C$_1$–C$_6$-alkylthio, C$_1$–C$_4$-halogenoalkylthio, benzyloxy which is optionally mono- to trisubstituted in the phenyl moiety by identical or different substituents from the group consisting of halogen and C$_1$–C$_6$-alkyl, or phenyl which is optionally mono- to trisubstituted by identical or different substituents from the group consisting of halogen, C$_1$–C$_6$-alkyl, C$_1$–C$_4$-halogenoalkyl, C$_1$–C$_6$-alkoxy, C$_1$–C$_4$-halogenoalkoxy, C$_1$–C$_6$-alkylthio, C$_1$–C$_4$-halogenoalkylthio, cyano, nitro and SCN.

R$^4$, R$^5$ and R$^6$ independently of one another each preferably represent hydrogen, C$_1$–C$_6$-alkyl, benzyl which is optionally mono- to trisubstituted in the phenyl moiety by identical or different substituents from the group consisting of halogen, C$_1$–C$_6$-alkyl and C$_1$–C$_6$-alkoxy, or preferably represent phenyl which is optionally mono- to trisubstituted by identical or different substituents from the group consisting of halogen, C$_1$–C$_6$-alkyl, C$_1$–C$_4$-halogenoalkyl, C$_1$–C$_6$-alkoxy, C$_1$–C$_4$-halogenoalkoxy, C$_1$–C$_6$-alkylthio, C$_1$–C$_4$-halogenoalkylthio, cyano, nitro and SCN, or R$^5$ and R$^6$ together represent C$_2$–C$_7$-alkanediyl which is optionally substituted by C$_1$–C$_6$-alkyl or phenyl (which is optionally substituted by halogen or C$_1$–C$_6$-alkyl).

A preferably represents a direct bond or NH.

X particularly preferably represents hydrogen or fluorine.

R particularly preferably represents one of the groups

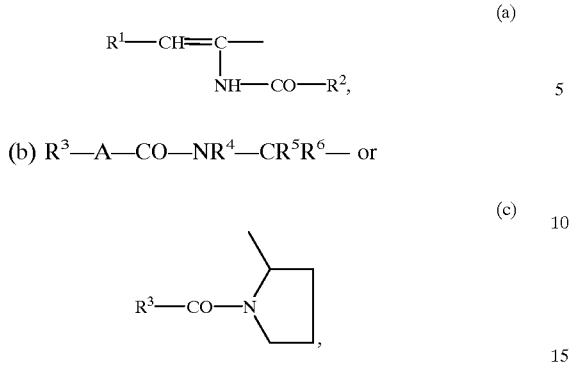

(a)

(b) $R^3$—A—CO—NR$^4$—CR$^5$R$^6$— or (c)

- $R^1$ particularly preferably represents $C_1$–$C_4$-alkyl or phenyl which is optionally mono- to trisubstituted by identical or different substituents from the group consisting of fluorine, chlorine, bromine, $C_1$–$C_4$-alkyl, $C_1$–$C_3$-halogenoalkyl having one to seven fluorine and/or chlorine atoms, $C_1$–$C_4$-alkoxy, $C_1$–$C_3$-halogenoalkoxy having one to seven fluorine and/or chlorine atoms, $C_1$–$C_4$-alkylthio, $C_1$–$C_2$-halogenoalkylthio having one to five fluorine and/or chlorine atoms, cyano and nitro, or particularly preferably represents thienyl, furanyl or pyridyl, each of which is optionally mono- or disubstituted by identical or different substituents from the group consisting of fluorine, chlorine, bromine, methyl and ethyl.
- $R^2$ particularly preferably represents $C_1$–$C_4$-alkyl, $C_1$–$C_2$-halogenoalkyl having one to five fluorine and/or chlorine atoms, or particularly preferably represents phenyl which is optionally mono- to trisubstituted by identical or different substituents from the group consisting of fluorine, chlorine, $C_1$–$C_4$-alkyl, $C_1$–$C_2$-halogenoalkyl having one to five fluorine and/or chlorine atoms, $C_1$–$C_4$-alkoxy, $C_1$–$C_2$-halogenoalkoxy having one to five fluorine and/or chlorine atoms, cyano and nitro.
- $R^3$ particularly preferably represents hydrogen, $C_1$–$C_4$-alkyl, $C_1$–$C_2$-halogenoalkyl having one to five fluorine and/or chlorine atoms, $C_2$–$C_4$-alkenyl, $C_1$–$C_4$-alkoxy, $C_1$–$C_2$-halogenoalkoxy having one to five fluorine and/or chlorine atoms, $C_1$–$C_4$-alkylthio, $C_1$–$C_2$-halogenoalkylthio having one to five fluorine and/or chlorine atoms, benzyloxy which is optionally mono- or disubstituted in the phenyl moiety by identical or different substituents from the group consisting of fluorine, chlorine, bromine and $C_1$–$C_4$-alkyl, or phenyl which is optionally mono- to trisubstituted by identical or different substituents from the group consisting of fluorine, chlorine, bromine, $C_1$–$C_4$-alkyl, $C_1$–$C_2$-halogenoalkyl having one to five fluorine and/or chlorine atoms, $C_1$–$C_4$-alkoxy, $C_1$–$C_2$-halogenoalkoxy having one to five fluorine and/or chlorine atoms, $C_1$–$C_4$-alkylthio, $C_1$–$C_2$-halogenoalkylthio having one to five fluorine and/or chlorine atoms, nitro and cyano.
- $R^4$, $R^5$ and $R^6$ independently of one another each particularly preferably represent hydrogen, $C_1$–$C_4$-alkyl, benzyl which is optionally mono- or disubstituted in the phenyl moiety by identical or different substituents from the group consisting of fluorine, chlorine, bromine, $C_1$–$C_4$-alkyl and $C_1$–$C_4$-alkoxy, or particularly preferably represent phenyl which is optionally mono- or disubstituted by identical or different substituents from the group consisting of fluorine, chlorine, bromine, $C_1$–$C_4$-alkyl and $C_1$–$C_4$-alkoxy, or
- $R^5$ and $R^6$ together represent optionally $C_1$–$C_4$-alkyl- or phenyl-substituted $C_2$–$C_5$-alkanediyl.
- A particularly preferably represents a direct bond or particularly preferably represents NH.
- X very particularly preferably represents hydrogen or fluorine.
- R very particularly preferably represents one of the groups

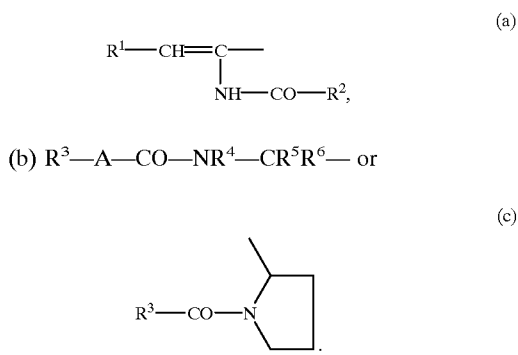

(a)

(b) $R^3$—A—CO—NR$^4$—CR$^5$R$^6$— or (c)

- $R^1$ very particularly preferably represents $C_1$–$C_3$-alkyl or phenyl which is optionally mono- or disubstituted by identical or different substituents from the group consisting of fluorine, chlorine, $C_1$–$C_3$-alkyl, $C_1$–$C_3$-halogenoalkyl having one to seven fluorine and/or chlorine atoms, $C_1$–$C_3$-alkoxy or $C_1$–$C_3$-halogenoalkoxy having one to seven fluorine and/or chlorine atoms, or very particularly preferably represents thienyl or furanyl, each of which is optionally monosubstituted by chlorine or methyl.
- $R^2$ very particularly preferably represents $C_1$–$C_3$-alkyl, trifluoromethyl or very particularly preferably represents phenyl which is optionally mono- or disubstituted by identical or different substituents from the group consisting of fluorine, chlorine and methyl.
- $R^3$ very particularly preferably represents hydrogen, $C_1$–$C_3$-alkyl, $C_2$–$C_4$-alkenyl, $C_1$–$C_3$-alkoxy, benzyloxy which is optionally monosubstituted in the phenyl moiety by fluorine, chlorine or methyl, or phenyl which is optionally mono- or disubstituted by identical or different substituents from the group consisting of fluorine, chlorine, methyl, trifluoromethyl, methoxy and trifluoromethoxy.
- $R^4$, $R^5$ and $R^6$ independently of one another each very particularly preferably represent hydrogen, $C_1$–$C_3$-alkyl, or very particularly preferably represents phenyl or benzyl, each of which is optionally mono- or disubstituted in the phenyl moiety by identical or different substituents from the group consisting of fluorine, chlorine and $C_1$–$C_3$-alkyl, or
- $R^5$ and $R^6$ together represent $C_2$–$C_5$-alkanediyl.
- A very particularly preferably represents a direct bond or very particularly preferably represents NH.

The abovementioned general or preferred radical definitions or illustrations apply to the end products and, correspondingly, to the starting materials and intermediates. These radical definitions can be combined with one another as desired, that is to say combinations between the respective preferred ranges are also possible.

Preference according to the invention is given to those compounds of the formula (I) which contain a combination of the definitions listed above as being preferred (preferable).

Particular preference according to the invention is given to those compounds of the formula (I) which contain a combination of the definitions listed above as being particularly preferred.

Very particular preference according to the invention is given to those compounds of the formula (I) which contain a combination of the definitions listed above as being very particularly preferred.

In the radical definitions mentioned hereinabove and hereinbelow, hydrocarbon radicals such as alkyl or alkenyl are—including in combination with hetero atoms such as alkoxy or alkylthio—straight-chain or branched as far as this is possible.

Using, for example. 2-methyl-4(-4-fluorobenzylidene)-oxazol-5-one and 3,4,4-trifluorobut-3-enol as starting materials for preparing compounds of the formula (I) according to process A), the course of the reaction can be illustrated by the following equation:

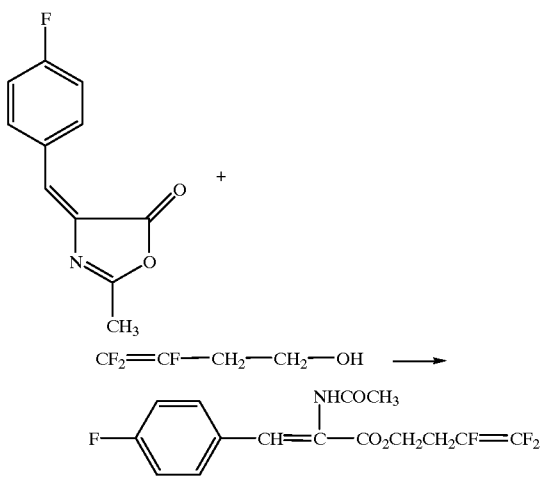

Using, for example, N-acetylglycine and 3,4,4-trifluorobut-3-enol as starting materials for preparing compounds of the formula (I) according to process Bα), the course of the reaction can be illustrated by the following equation:

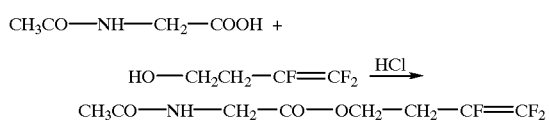

Using, for example, 2-methyl-oxazol-5-one and 3,4,4-trifluorobut-3-enol as starting materials for preparing compounds of the formula (I) according to process Bβ), the course of the reaction can be illustrated by the following equation:

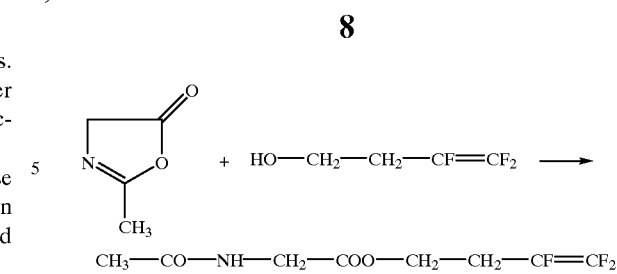

Using, for example, N-benzyloxycarbonylproline and 3,4,4-trifluorobut-3-enol as starting materials for preparing compounds of the formula (I) according to process C), the course of the reaction can be illustrated by the following equation:

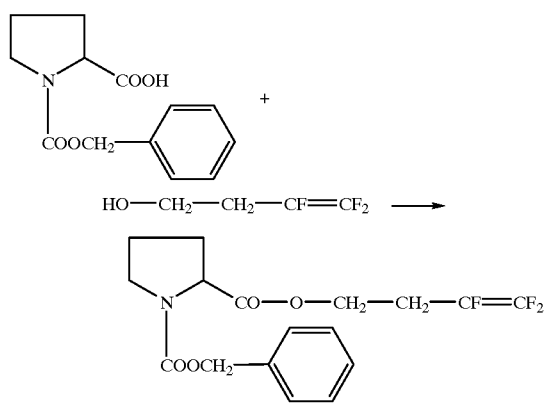

The above-described process A) for preparing compounds of the formula (Ia) is characterized in that aziactones of the formula (II) are reacted with alcohols of the formula (III), if appropriate in the presence of a diluent and, if appropriate, in the presence of a base.

The process A) according to the invention is preferably carried out in the presence of a diluent.

Suitable diluents are in particular organic solvents, for example optionally chlorinated aliphatic or aromatic hydrocarbons such as cyclohexane, toluene, xylene, dichloromethane, dichloroethane, chloroform, chlorobenzene or dichlorobenzene, ethers such as dioxane or tetrahydrofuran, nitriles such as acetonitrile, sulphoxides such as dimethyl sulphoxide, amides such as dimethylformamide, dimethylacetamide or N-methylpyrrolidone, and also sulpholane.

Suitable bases are organic and inorganic bases.

Preference is given to using amines, in particular tertiary amines such as triethylamine, diazabicycloundecene (DBU), diazabicyclononene (DBN), diazabicyclooctane (DABCO) or pyridine or alkali metal or alkaline earth metal carbonates, bicarbonates or hydroxides. Examples include sodium carbonate, potassium carbonate, sodium bicarbonate, sodium hydroxide, potassium hydroxide and calcium hydroxide.

The reaction temperature in process A) can be varied within a relatively wide range. In general, the reaction is carried out at temperatures between 10° C. and 200° C., preferably between 20° C. and 160° C.

The molar ratio of the compound of the formula (II) to the compound of the formula (III) is generally 3:1 to 1:3, preferably 1.5:1 to 1:1.5.

The reaction is generally carried out under atmospheric pressure.

For work-up, the reaction mixture is for example hydrolyzed and the product is extracted with an organic solvent such as ethyl acetate, dichloromethane or toluene, or the crude product is chromatographed.

The specifications of process A) apply correspondingly to the practice of the process Bβ) according to the invention.

The above-described process Bα) and the process C) for preparing compounds of the formula (Ib) and (Ic), respectively, are characterized in that acylated amino acids of the formula (IV) or (III), respectively, are reacted with alcohols of the formula (II), if appropriate in the presence of a diluent and in the presence of a reactive reagent.

Such esterification reactions have been known for a long time and are described, for example, in Houben-Weyl, Methoden der organischen Chemie, Georg Thieme Verlag, Stuttgart, 1974, Volume XV/1, p. 315 ff, which is expressly incorporated herein by reference.

The compounds of the formulae (Ib) and (Ic) can also be prepared, for example, by reacting salts (for example alkali metal salts such as sodium salts or potassium salts) of the acylated amino acids of the formulae (IV) and (VI) with a fluorobutenyl bromide of the formula (VII)

$$CF_2=CX-CH_2-CH_2-Br \qquad (VII)$$

in which

X is as defined above, in the presence of a diluent (for example dimethylformamide, dimethyl sulphoxide, sulpholane, dioxane or acetonitrile) (cf. the Preparation Examples).

The azlactones of the formulae (II) and (V) required as starting materials for the processes A) and Bβ), respectively, are known and/or can be prepared in a simple manner by known methods (cf. the Preparation Examples).

The acylated amino acids of the formulae (IV) and (VI) required as starting materials in the processes Bα) and C) are known and/or can be prepared in a simple manner, for example by acylation of the corresponding amino acids (cf. Houben-Weyl, Methoden der organischen Chemie, Georg Thieme Verlag. Stuttgart 1974, Volume XV/1, p. 46 ff.).

The alcohols of the formula (III) required as starting materials are known (see for example WO 92/15 555).

The fluorobutenyl bromides of the formula (VII) are known and/or can be prepared in a simple manner by known processes (cf. C.A. 119, 94 942).

The active compounds are suitable for controlling animal pests, in particular insects, arachnids and nematodes, encountered in agriculture, in forests, in the protection of stored products and of materials, and in the hygiene sector. They can preferably be employed as crop protection agents. They are active against normally sensitive and resistant species and against all or some stages of development. The abovementioned pests include:

From the order of the Isopoda, for example, Oniscus asellus, Armadillidium vulgare and Porcellio scaber.

From the order of the Diplopoda, for example, Blaniulus guttulatus.

From the order of the Chilopoda, for example, Geophilus carpophagus and Scutigera spec.

From the order of the Symphyla, for example, Scutigerella immaculata.

From the order of the Thysanura, for example, Lepisma saccharina.

From the order of the Collembola, for example, Onychiurus armatus.

From the order of the Orthoptera, for example, Blatta orientalis, Periplaneta americana Leucophaea maderae, Blattella germanica, Acheta domesticus, Gryllotalpa spp., Locusta migratoria migratorioides, Melanoplus differentialis and Schistocerca gregaria.

From the order of the Dermaptera, for example, Forficula auricularia.

From the order of the Isoptera, for example, Reticulitermes spp.

From the order of the Anoplura, for example, Pediculus humanus corporis, Haematopinus spp. and Linognathus spp.

From the order of the Mallophaga, for example, Trichodectes spp. and Damalinea spp.

From the order of the Thysanoptera, for example, Hercinothrips femoralis and Thrips tabaci.

From the order of the Heteroptera, for example, Euryga-ster spp., Dysdercus intermedius, Piesma quadrata, Cimex lectularius, Rhodnius prolixus and Triatoma spp.

From the order of the Homoptera, for example, Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus spp., Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. and Psylla spp.

From the order of the Lepidoptera, for example, Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Spodoptera litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima and Tortrix viridana.

From the order of the Coleoptera, for example, Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis and Costelytra zealandica.

From the order of the Hymenoptera, for example, Diprion spp., Hoplocampa spp., Lasius spp., Monomorium pharaonis and Vespa spp.

From the order of the Diptera, for example, Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae and Tipula paludosa.

From the order of the Siphonaptera, for example, Xenopsylla cheopis and Ceratophyllus spp.

From the order of the Arachnida, for example, *Scorpio maurus* and *Latrodectus mactans*.

From the order of the Acarina, for example, *Acarus siro*, Argas spp., Omithodoros spp. *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include, for example, Pratylenchus spp., *Radopholus similis, Ditylenchus dipsaci, Tylenchulus semipenetrans*, Heterodera spp., Globodera spp., Meloidogyne spp., Aphelenchoides spp., Longidorus spp., Xiphinema spp. and Trichodorus spp.

The compounds of the formula (I) according to the invention in particular have outstanding nematicidal activity, for example against *Meloidogyne incognita*.

Some of the active compounds according to the invention also act systemically, in particular at relatively high application rates, and can be applied via the leaves, if appropriate.

The active compounds can be converted to the customary formulations, such as solutions, emulsions, wettable powders, suspensions, powders, dusting agents, pastes, soluble powders, granules, suspo-emulsion concentrates, natural and synthetic materials impregnated with active compound and very fine capsules in polymeric substances.

These formulations are produced in a known manner, for example by mixing the active compounds with extenders, that is liquid solvents and/or solid carriers, if appropriate with the use of surfactants, that is emulsifiers and/or dispersants and/or foam-formers.

In the case of the use of water as an extender, organic solvents can, for example, also be used as auxiliary solvents. Essentially, the following are suitable liquid solvents: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are:

for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Possible further additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous mixing components are the following:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol folpet, fosetylaluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon,
quintozene (PCNB),
sulphur and sulphur preparations,
tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole,
validamycin A, vinclozolin,
zineb, ziram.
Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.
Insecticides/Acaricides/Nematicides:
abamectin, AC 303 630, acephate, acrinathrin, alanycarb, aldicarb, alphamethrin, amitraz, avermectin, AZ 60541, azadirachtin, azinphos A, azinphos M, azocyclotin,
Bacillus thuringiensis, bendiocarb, benfuracarb, bensultap, beta-cyfluthrin, bifenthrin, BPMC, brofenprox, bromophos A, bufencarb, buprofezin, butocarboxim, butylpyridaben,
cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylyinphos, dioxathion, disulfoton,
edifenphos, emamectin, esfenvalerate, ethiofencarb, ethion, ethofenprox, ethoprophos, etrimfos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin,
lambda-cyhalothrin, lufenuron,
malathion, mecarbam, mevinphos, mesulfenphos, metaldehyde, methacrifos, methamidophos, methidathion, methiocarb, methomyl, metolcarb, milbemectin, monocrotophos, moxidectin,
naled, NC 184, NI 25, nitenpyram,
omethoate, oxamyl, oxydemeton M, oxydeprofos,
parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozine, pyrachlophos, pyradaphenthion, pyresmethrin, pyrethrum, pyridaben, pyrimidifen, pyriproxyfen,
quinalphos,
RH 5992,
salithion, sebufos, silafluofen, sulfotep, sulprofos,
tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb,
vamidothion, XMC, xylylcarb, YI 5301/5302, zetamethrin.

A mixture with other known active compounds, such as herbicides, or with fertilizers and growth-regulators is also possible.

The active compounds according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene and stored-product pests, the active compound has excellent residual action on wood and clay and good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the sub-orders Amblycerina and Ischnocerina, for example, Trimenopon spp., Menopon spp., Trinoton spp., Bovicola spp. Werneckiella spp., Lepikentron spp., Damalina spp., Trichodectes spp. and Felicola spp.

From the order Diptera and the sub-orders Nematocerina and Brachycerina. for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, Blatta orientalis, *Periplaneta americana, Blattela germanica* and Supella spp.

From the sub-class of the Acaria (Acarida) and the orders of the Meta- and Mesostigmata, for example, Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

For example, they have a good development inhibitory activity against *Lucilla cuprina* fly larvae.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, caged birds, aquarium fish, and so-called experimental animals, such as, for example, hamsters, guinea-pigs, rats and mice. By controlling these arthropods, it is intended to reduce mortality and decreased performances (in meat, milk. wool, hides, eggs, honey and the like), so that more economical and simpler animal keeping is possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal administration, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, directly or after dilution by a factor of 100 to 10,000, or they may be used in the form of a chemical bath.

The preparation and the use of the active compounds according to the invention are illustrated by the examples below.

PREPARATION EXAMPLES

Example Ia-1

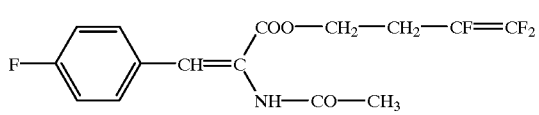

8.2 g (40 mmol) of 2-methyl-4-(4-fluorobenzylidene)-oxazol-5-one of Example (II-1) in 100 ml of toluene are heated overnight under reflux with 6.3 g (50 mmol) of 3,4,4-trifluorobut-3-enol, with the addition of 200 mg of 4-dimethylaminopyridine. After cooling, the solution is washed with water and concentrated under reduced pressure and the brown solid is chromatographed over silica gel using the system chloroform/ethyl acetate (4:1). 6.5 g (Yield 49% of theory) of 3,4,4-trifluorobut-3-enyl 3-(4-fluorophenyl)-2-acetylamino-prop-2-enoate of mp.: 116° are obtained.

By a similar method and/or according to the general preparation procedures, the following compounds of the formula (Ia) are obtained:

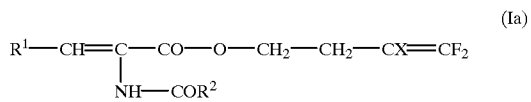

(Ia)

| Ex. No. | X | R¹ | R² | Physic. Data |
|---|---|---|---|---|
| Ia-2 | F | phenyl | CH₃ | mp.: 94° C. |
| Ia-3 | F | 4-Cl-phenyl | CH₃ | mp.: 142° C. |
| Ia-4 | F | 2-thienyl | CH₃ | mp.: 84° C. |
| Ia-5 | F | 2-thienyl | phenyl | mp.: 116° C. |
| Ia-6 | F | 4-Cl-phenyl | phenyl | mp.: 140° C. |
| Ia-7 | F | 4-CH₃-phenyl | CH₃ | mp.: 118° C. |
| Ia-8 | F | 4-F-phenyl | CH₃ | mp.: 116° C. |
| Ia-9 | F | 4-OCF₃-phenyl | CH₃ | mp.: 62° C. |
| Ia-10 | F | 3,4-diCl-phenyl | CH₃ | mp.: 142° C. |
| Ia-11 | F | phenyl | phenyl | mp.: 126° C. |

Example Ib-1

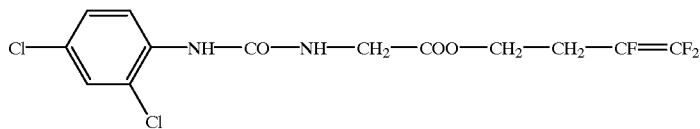

4.5 g (17.1 mmol) of N-(2,4-dichlorophenyl)aminocarbonyl)-glycine and 2.2 g (17.6 mmol) of 3,4,4-trifluorobut-3-enol are dissolved in 50 ml of tetrahydrofuran. At 0° C., 5.2 g (40 mmol) of ethyl-diisopropylamine are added and, after 5 minutes, 5.2 g (20 mmol) of bis-(2-oxo-3-oxazolidinyl)-phosphinic chloride are added with stirring. The mixture is stirred overnight and then poured into water, the product is extracted with ethyl acetate and the crude product is purified by column chromatography over silica gel using the system ethyl acetate. 0.3 g (4.8% of theory) of colourless crystals of 3,4,4-trifluorobut-3-enyl N-((2,4-dichlorophenyl)aminocarbonyl)glycinate of mp.: 120° C. are obtained.

Example Ib-2

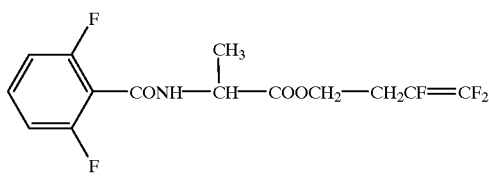

6.4 g (28 mmol) of N-(2,6-difluorobenzoyl)alanine are dissolved in 50 ml of dimethyl sulphoxide (DMSO) and admixed with 1.2 g (31 mmol) of sodium hydroxide dissolved in a little water. 5.7 g (30 mmol) of 3,4,4-trifluorobut-3-enyl bromide are subsequently added, and the mixture is stirred at 20° C. overnight. The mixture is then poured into water and the product is extracted with ethyl acetate and subsequently purified by column chromatography over silica gel using the system ethyl acetate. In this manner, 2.5 g (26.5% of theory) of 3,4,4-trifluorobut-3-enyl N-(2,6-difluorobenzoyl)-alaninate are obtained as an oil. log p (pH 2)=2.42.

By a similar method and/or according to the general procedures, the following compounds of the formula (Ib) are obtained

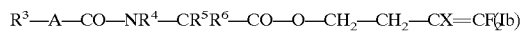

| Ex. No. | X | A | $R^3$ | $R^4$ | $R^5$ | $R^6$ | Physic. Data |
|---|---|---|---|---|---|---|---|
| Ib-3 | F | NH | ![3,4-dichlorophenyl] | H | H | H | mp.: 98–102° C. |
| Ib-4 | F | — | $CH_3$ | H | ![4-methylphenyl] | H | mp.: 98–100° C. |
| Ib-5 | F | — | ![4-chlorophenyl] | H | $-CH_2-$![phenyl] | H | mp.: 92° C. |
| Ib-6 | F | — | ![phenyl] | H | H | H | log p (pH 2) = 2.09 |

-continued

| Ex. No. | X | A | R³ | R⁴ | R⁵ | R⁶ | Physic. Data |
|---|---|---|---|---|---|---|---|
| Ib-7 | F | — | 4-Cl-C₆H₄- | H | —CH₂—CH₂— | | mp.: 128–130° C. |
| Ib-8 | F | — | CH₃ | H | CH₃ | H | mp.: 46° C. |
| Ib-9 | F | — | CH₃ | H | —CH₂—CH₂— | | mp.: 82° C. |
| Ib-10 | F | — | CH₂=CH | H | H | H | mp.: 122° C. |
| Ib-11 | F | — | 4-Cl-C₆H₄- | H | CH₃ | H | mp.: 58° C. |
| Ib-12 | F | — | 4-Cl-C₆H₄- | H | H | H | mp.: 66° C. |
| Ib-13 | F | — | CH₃ | H | C₆H₅- | H | mp.: 72° C. |
| Ib-14 | F | — | H | H | —CH₂—CH₂— | | log p (pH 2) = 1.32 |
| Ib15 | F | — | 4-Cl-C₆H₄- | H | H | CH₃ | mp: 40° C. | and of the formula (Ic)

(Ic)

[pyrrolidine structure with N-COR³ and CO—O—CH₂—CH₂—CX=CF₂]

| Ex. No. | X | R³ | Physic. Data |
|---|---|---|---|
| Ic-1 | F | —O—CH₂—C₆H₅ | log p (pH 2) = 3.31 |

Example II-1

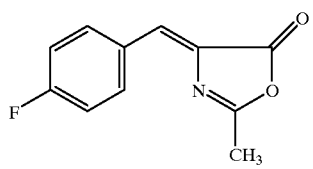

With stirring, 7.5 g (0.1 mol) of glycine with 6.2 g (0.075 mol) of anhydrous sodium acetate and 18.6 g (0.15 mol) of p-fluorobenzaldehyde in 60 ml of acetic anhydride are heated to 100° C. After 2 hours, the reaction is cooled and poured into water. The resulting precipitate is filtered off with suction and dried under reduced pressure. 12.1 g (59% of theory) of 2-methyl-4-(4-fluorobenzylidene)-oxazol-5-one of mp. 156° C. are obtained.

USE EXAMPLE

Example A

Critical Concentration Test/nematodes

Test nematode: Meloidogyne incognita

Solvent: 4 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The active compound preparation is intimately mixed with soil which is heavily infested with the test nematodes. The active compound concentration in the preparation is immaterial, only the amount of active compound per unit volume of soil, which is given in ppm (=mg/l), matters. The treated soil is transferred into pots, lettuce is sown in, and the pots are kept at a greenhouse temperature of 25° C.

After four weeks, the lettuce roots are checked for infestation with nematodes (root galls) and the efficacy of the active compound in % is determined. The efficacy is 100% when infestation is avoided completely and 0% when the infestation level is just as high as in the control plants in untreated, but equally infested, soil.

In this test, an efficacy of 100% was shown, for example, by the compound of Preparation Example Ia-2, at an exemplary active compound concentration of 20 ppm.

Example B

Test with *Boophilus Microplus* Resistent/SP-resistent Parkhurst Strain

Test animals: Adult females which have sucked themselves full

Solvent: Dimethyl sulphoxide 20 mg of active compound are dissolved in 1 ml of dimethyl sulphoxide, and lower concentrations are prepared by diluting in the same solvent.

The test is carried out in 5 replications. 1 μl of the solutions is injected into the abdomen, and the animals are transferred into dishes and kept in an air-conditioned room. The activity is determined via the inhibition of oviposition. 100% means that no tick has deposited eggs.

In this test, an activity of 100% was shown, for example, by the compound of Preparation Example Ia-4, at an exemplary active compound concentration of 20 μg/animal.

We claim:

1. Compounds of the formula (I)

R—CO—O—CH$_2$—CH$_2$—CX=CF$_2$    (I)

in which

X represents hydrogen or halogen and

R represents one of the groups (a)
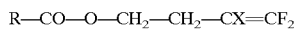
R$^1$—CH=C—
          |
          NH—CO—R$^2$, (b) R$^3$—A—CO—NR$^4$—CR$^5$R$^6$— or (c)
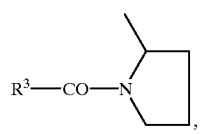
R$^3$—CO—N in which R$^1$ represents respectively optionally substituted alkyl, aryl or hetaryl, R$^2$ represents hydrogen, alkyl, halogenoalkyl or optionally substituted aryl, R$^3$ represents hydrogen, alkyl, halogenoalkyl, alkenyl, alkoxy, halogenoalkoxy, alkylthio, halogenoalkylthio or respectively optionally substituted aralkyloxy or aryl, R$^4$, R$^5$ and R$^6$ independently of one another each represent hydrogen. alkyl or respectively optionally substituted aralkyl or aryl, or R$^5$ and R$^6$ together represent optionally substituted alkanediyl and A represents a direct bond or represents NH.

2. Process for preparing compounds of the formula (I) according to claim 1, wherein (A) the compounds of the formula (Ia) are obtained when azlactones of the formula (II)

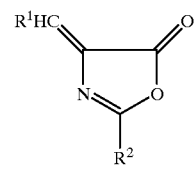
(II)

in which

R$^1$ and R$^2$ are each as defined in claim 1 are reacted with alcohols of the formula (III)

CF$_2$=CX—CH$_2$—CH$_2$—OH    (III)

in which

X is as defined in claim 1, in the presence of a diluent and, if appropriate, in the presence of a base, (B) the compounds of the formula (Ib) are obtained when α) acylated amino acids of the formula (IV)

R$^3$—A—CO—NR$^4$—CR$^5$R$^6$—COOH    (IV)

in which

A, R$^3$, R$^4$, R$^5$ and R$^6$ are each as defined in claim 1 are reacted with alcohols of the formula (III)

CF$_2$=CX—CH$_2$—CH$_2$—OH    (III)

in which

X is as defined above, if appropriate in the presence of a diluent and in the presence of a reactive reagent, or β) azlactones of the formula (V)

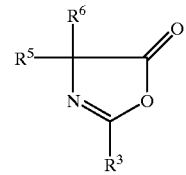
(V)

in which

R$^3$, R$^5$ and R$^6$ are each as defined above are reacted with alcohols of the formula (III)

CF$_2$=CX—CH$_2$—CH$_2$—OH    (III)

in which

X is as defined above, in the presence of a diluent and, if appropriate, in the presence of a base, (C) compounds of the formula (Ic) are obtained when acylated amino acids of the formula (VI)

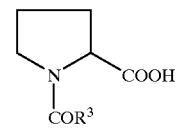
(VI)

in which $R^3$ is as defined above
are reacted with alcohols of the formula (III)

$$CF_2=CX-CH_2-CH_2-OH \quad (III)$$

in which
X is as defined above,
if appropriate in the presence of a diluent and in the presence of a reactive reagent.

3. A pesticidal composition comprising a pesticidally effective amount of a according to claim 1 and a diluent.

4. A method of combating unwanted pests which comprises administering to such pests or to a locus from which it is desired to exclude such pests a pesticidally effective amount of a compound according to claim 1.

* * * * *